(12) United States Patent
Stephens et al.

(10) Patent No.: US 10,232,062 B2
(45) Date of Patent: Mar. 19, 2019

(54) RADIOLABELLED MATERIAL

(71) Applicant: The Australian National University, Acton (AU)

(72) Inventors: Ross Wentworth Stephens, Stirling (AU); Jessica Louise Bell, Queanbeyan (AU)

(73) Assignee: The Australian National University, Acton, ACT (AU)

( * ) Notice: Subject to any disclaimer, the term of this patent is extended or adjusted under 35 U.S.C. 154(b) by 6 days.

(21) Appl. No.: 14/901,633

(22) PCT Filed: Dec. 20, 2013

(86) PCT No.: PCT/AU2013/001510
§ 371 (c)(1),
(2) Date: Dec. 28, 2015

(87) PCT Pub. No.: WO2015/000012
PCT Pub. Date: Jan. 8, 2015

(65) Prior Publication Data
US 2016/0151518 A1 Jun. 2, 2016

Related U.S. Application Data

(60) Provisional application No. 61/841,921, filed on Jul. 1, 2013.

(51) Int. Cl.
*A61K 51/06* (2006.01)
*A61K 51/12* (2006.01)
*A61K 51/00* (2006.01)
*A61K 51/02* (2006.01)

(52) U.S. Cl.
CPC ........ *A61K 51/065* (2013.01); *A61K 51/1244* (2013.01); *A61K 51/1251* (2013.01); *A61K 51/00* (2013.01); *A61K 51/02* (2013.01); *A61K 51/06* (2013.01)

(58) Field of Classification Search
None
See application file for complete search history.

(56) References Cited

U.S. PATENT DOCUMENTS

| 5,593,658 A * | 1/1997 | Bogdanov ........ A61K 47/48215 424/9.34 |
| 5,762,903 A | 6/1998 | Park et al. |
| 7,192,395 B1 | 3/2007 | Qu et al. |
| 2001/0006616 A1 | 7/2001 | Leavitt et al. |
| 2002/0054851 A1 | 5/2002 | Grunze et al. |
| 2003/0120355 A1 | 6/2003 | Hafeli et al. |
| 2004/0258614 A1 | 12/2004 | Line et al. |
| 2006/0067883 A1 | 3/2006 | Krom et al. |
| 2008/0166297 A1 | 7/2008 | Ryu et al. |
| 2008/0305042 A1 | 12/2008 | Gacek et al. |
| 2009/0169471 A1 | 7/2009 | Richard et al. |
| 2010/0251856 A1 * | 10/2010 | Santhanam ........... B22F 1/0018 75/370 |
| 2011/0165070 A1 * | 7/2011 | Stephens ............ A61K 41/0095 424/1.21 |

FOREIGN PATENT DOCUMENTS

| WO | 2005/061009 A2 | 7/2005 |
| WO | 2009/067767 A2 | 6/2009 |
| WO | 2009-110939 A9 | 9/2009 |
| WO | 2014-197940 A1 | 12/2014 |

OTHER PUBLICATIONS

International Search Report and Written Opinion dated Mar. 25, 2014 for PCT/AU2013/001510, 7 pages.
Gardner et al., "The Iodination of Phenols and the Iodometric Estimation of, and Action of Reducing Agents on, Tannic Acid." 1909, *J. Chem. Soc., Trans.* 95:1819-1827.
Kraal, P. et al., "Copper complexation by tannic acid in aqueous solution," 2006, *Chemosphere* 65: 2193-2198.
McDonald et al, "Precipitation of Metal Ions by Plant Polyphenols: Optimal Conditions and Origin of Precipitation," 1996, *J. Agric. Food Chem.* 44:599-606.
*Kirk-Othmer Concise Encyclopedia of Chemical Technology*, 1985, pp. 665-666, 3rd edition, John Wiley and Sons.

* cited by examiner

*Primary Examiner* — James W Rogers
(74) *Attorney, Agent, or Firm* — Kilpatrick Townsend & Stockton LLP

(57) ABSTRACT

The invention relates to a radiolabelled material comprising a polymer, a radioactive isotope, and an immobilizing agent, wherein the immobilizing agent is capable of immobilizing the radioactive isotope on or in the polymer, and wherein the immobilizing agent is a macromolecule comprising electron donating groups. The invention also relates to a process for making a radiolabelled material, to use of a radiolabelled material for the preparation of medicaments for treating cancer and/or for radiation imaging, and to use of a radiolabelled material in the treatment of cancer. There is further described use of an immobilizing agent to immobilize a radioactive isotope on or in a polymer.

17 Claims, 1 Drawing Sheet

RADIOLABELLED MATERIAL

INCORPORATION BY CROSS REFERENCE

This application claims priority from U.S. patent application No. 61/841,921 filed on 1 Jul. 2013, the entire contents of which are incorporated herein by cross reference.

TECHNICAL FIELD

The present invention relates to the preparation of radiolabelled materials, such as radiolabelled polymers for use in medical applications. In particular, the present invention relates to the use of radiolabelled materials in regional and targeted radiotherapy, and in radioactive imaging.

BACKGROUND

The local administration of radioactive materials may be used as a treatment for cancer, and in particular for cancers which cannot be treated surgically. The radioactive materials are incorporated into devices such as microparticles, seeds and wires which are directly implanted into the cancer.

Selective internal radiation therapy (SIRT) is a form of radiation therapy which involves injecting microspheres of radioactive material into the arteries that supply the tumour.

For example, the resin based "SIR-spheres®" (SIR-spheres® is a registered trademark of Sirtex SIR-Spheres Pty Ltd) microspheres carry the $^{90}$Y isotope and are used for SIRT. $^{90}$Y is very suitable for beta radiation therapy as tumor cells are killed within a radius of 1 to 2 mm. However, beta radiation is very poor for imaging. Bremsstrahlung imaging (which uses a photon produced by the deceleration and subsequent loss of kinetic energy when the particles produced during beta decay are deflected by other charged particles in the tissue) is not very accurate as it is not a true representation of where the isotope actually is and gives poor resolution images. Therefore, it can be difficult to ascertain whether the radiation has been successfully delivered to the target organ and to what extent.

In order to solve the problem of poor imaging, "mimic" microparticles may be administered to the patient as an investigative procedure before the administration of any therapeutic microspheres. The mimic microspheres have a similar median particle diameter but are composed of a different material to the therapeutic microspheres, and may be labeled with Tc-99m which is suitable for gamma imaging techniques. For example, heat-aggregated albumin (MAA) labeled with Tc-99m (Tc99m-MAA) may be administered to liver cancer patients as an investigative procedure before any therapeutic microspheres are administered. An image of the distribution of the mimic particles from the hepatic artery is obtained from which it can be predicted where therapeutic microspheres are likely to be distributed. If an appreciable level of Tc99m-MAA is found to leave the liver rather than remaining near the tumor, then the risk of radiation exposure to surrounding healthy organs is too large and the therapeutic microspheres are either not administered or the patient receives a reduced dose.

However, mimic particles do not always accurately predict the distribution of the therapeutic particles, which can lead to an overestimate in the number of patients deemed unsuitable for therapeutic microspheres.

Existing treatments also present the following problems. The radioactive elements often have short half-lives, and the time elapsed between the manufacture of the radioactive material and the administration to the patient may result in significant loss of activity. This in turn leads to high costs associated with manufacture and transportation of the radioactive materials to the hospital and patient.

Incomplete retention of the radionuclide on the device can result in leaching of the radionuclide into healthy, non-cancerous tissues before reaching the target organ. It is therefore desirable to have the maximum control over the dosing of the radiation as possible, in order to deliver the radiation to the target organ in preference to healthy tissues.

The radioactive material can often only accommodate one particular radioactive element, rather than two or more radioactive elements, which can restrict the versatility of the treatment program.

It is therefore an object of the invention to provide a radiolabelled material for the treatment of cancer, which overcomes the above problems. In particular, it is desirable to develop a method by which the subsequent organ distribution of therapeutic microspheres may be more accurately predicted. Further, if therapeutic microspheres are administered, it is desirable to have a reliable method for determining the precise site of radiation exposure in the patient's body in order to determine the effectiveness of the treatment and the necessity for future treatments.

SUMMARY OF THE INVENTION

In a first aspect of the invention, there is provided a radiolabelled material comprising:
  (i) a polymer;
  (ii) a radioactive isotope; and
  (iii) an immobilizing agent;
wherein the immobilizing agent is capable of immobilizing the radioactive isotope on or in the polymer, and wherein the immobilizing agent is a macromolecule comprising electron donating groups.

In an embodiment, the electron donating groups comprise at least one of O, N, S and P. In an embodiment, the electron donating groups are —OH. In an embodiment, the immobilizing agent is a phenol or polyphenol compound. In an embodiment, the immobilizing agent is selected from tannins, tannic acid and theaflavin-3-gallate. In an embodiment, the polymer is a synthetic polymer. In an embodiment, the synthetic polymer is a cationic exchange resin comprising at least one of a sulfate, sulfonate, carboxylate and phosphate group. In an embodiment, the polymer is polystyrene sulfonate.

In an embodiment, the polymer is in the form of particulate microspheres having a median diameter of between 2 and 200 microns. In an embodiment, the particulate microspheres have a median diameter of 10 to 50 microns. In an embodiment, the particulate microspheres have a median diameter of up to 35 microns. In an embodiment, the particulate microspheres have a median diameter of 25 to 35 microns.

In an embodiment, the radioactive isotope enables imaging and/or therapy. In an embodiment, the imaging includes SPECT imaging, and/or PET imaging. In an embodiment, the radioactive isotope is selected from Ac-225, At-211, Au-198, Bi-212, Bi-213, Co-57, Cr-51, Cu-64, Cu-67, Dy-165, Er-169, F-18, Fe-59, Ga-67, Ga-68, Gd-153, Ho-166, I-123, I-124, I-125, I-131, I-132, In-111, Ir-192, Lu-177, Pd-103, Rb-81, Rb-86, Re-186, Re-188, Ru-103, Sc-47, Sm-153, Sn-117m, Sr-89, Tb-161, Tc-99m, Tl-201, Y-90, Yb-169 and Zr-89. In an embodiment, the radioactive isotope is selected from Group XIII of the periodic table. In an embodiment, the radioactive isotope is Ga-67, In-111, Lu-177, Tl-201 or Y-90.

In an embodiment, the radiolabelled material according to first aspect comprises a combination of at least two radioactive isotopes to enable imaging and/or therapy. In an embodiment, the combination of radioactive isotopes is selected from Ga-68 and Lu-177; Ga-67 and Y-90; Ga-68 and Y-90; In-111 and Y-90; Tl-201 and Y-90; Lu-177 and Y-90 and Ga-67 and Tb-161. In an embodiment, the polymer and/or immobilizing agent is radiolabelled to enable imaging and/or therapy. In an embodiment, the imaging includes SPECT imaging and/or PET imaging. In an embodiment, the radiolabel is I-123, I-124, I-125, I-131, I-132, F-18 and/or At-211. In an embodiment, the radiolabel is I-131. In an embodiment, the polymer and/or immobilizing agent is radiolabelled with I-123 for imaging and the radioactive isotope is Y-90 for therapy. In an embodiment, the radioactive isotope is Y-90 and the polymer and/or immobilizing agent is radiolabelled with I-123, I-131 or F-18; the radioactive isotope is Lu-177 and the polymer and/or immobilizing agent is radiolabelled with F-18; or the radioactive isotope is Tb-161 and the polymer and/or immobilizing agent is radiolabelled with F-18.

In an embodiment, the radiolabelled material according to the first aspect above further comprises at least one non-radioactive carrier metal. In an embodiment, the non-radioactive carrier metal is selected from Bi, Fe, Ga and Y. In an embodiment, the non-radioactive carrier metal enables MRI imaging and/or X-ray contrast imaging. In an embodiment, the non-radioactive carrier metal is Fe to enable MRI imaging and/or the non-radioactive carrier metal is Bi to enable X-ray contrast imaging. In an embodiment, the radioactive isotope emits gamma, beta and/or positron radiation.

In a second aspect of the invention, there is provided a process for making a radiolabelled material according to the first aspect above comprising:
(i) mixing the polymer as described in the first aspect above with a radioactive isotope as described in the first aspect above;
(ii) optionally washing the resulting mixture;
(iii) further adding an immobilizing agent as described in the first aspect above; and
(iv) optionally washing the resulting mixture.

In a third aspect of the invention, there is provided use of an immobilizing agent to immobilize a radioactive isotope on or in a polymer, wherein the immobilizing agent, the radioactive isotope and the polymer are according to the first aspect of the invention.

In a fourth aspect of the invention, there is provided use of the radiolabelled material according to the first aspect of the invention for the manufacture of a medicament for the treatment of cancer and/or for radiation imaging.

In a fifth aspect Of the invention, there is provided a method for the treatment of cancer, the method comprising administering an effective amount of the radiolabelled material according to the first aspect of the invention to a patient in need thereof.

In an embodiment, the cancer is primary or secondary liver cancer or primary kidney cancer (renal carcinoma).

In a sixth aspect of the invention, there is provided a medical device comprising the radiolabelled material according to the first aspect of the invention.

In a seventh aspect of the invention, there is provided a medical device according to the sixth aspect of the invention, which is a microsphere, seed, stent, catheter, wire or wafer.

In an eighth aspect of the invention, there is provided a radiolabelled material according to the first aspect above for use in therapy.

In a ninth aspect of the invention, there is provided a radiolabelled material according to the first aspect above for use in the treatment of cancer.

In a tenth aspect of the invention, there is provided a radiolabelled material according to the first aspect above for use in radiation imaging.

DEFINITIONS

Figure 1:
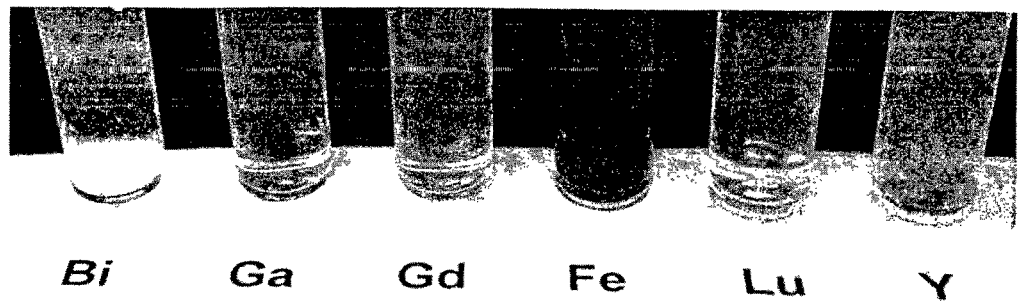
FIG. 1 shows the results of adding 1.0 M solutions (15 µL) of metal chloride salts (all from Sigma-Aldrich) in 1.0 M HCl, where the metals are bismuth (Bi), gallium (Ga), gadolinium (Gd), iron (Fe), lutetium (Lu), and yttrium (Y), to a 3 mM solution of tannic acid (5 mL; Sigma-Aldrich) at room temperature. Bismuth ions immediately formed a heavy cream precipitate; ferric ions immediately formed a heavy blue-black colloid, and yttrium ions at first gave no visible change, but within 3 min formed a grey turbid colloid. Gallium, gadolinium and lutetium ions showed no change, even on long standing.

As used in this application, the singular form "a", "an" and "the" include plural references unless the context clearly dictates otherwise. For example, the phrase "a radioisotope" also includes a plurality of radioisotopes.

As used herein, the term "comprising" means "including." Variations of the word "comprising", such as "comprise" and "comprises," have correspondingly varied meanings. Thus, for example, a radiolabelled material "comprising" a polymer, a radioactive isotope and an immobilizing agent may consist exclusively of that polymer, radioactive isotope and immobilizing agent or may include one or more additional components (e.g. a carrier metal).

It will be understood that use of the term "between" herein when referring to a range of numerical values encompasses the numerical values at each endpoint of the range. For example, a microsphere having a median diameter of between 2 and 200 microns is inclusive of a microsphere having a median diameter of 2 microns and microsphere having a median diameter of 200 microns.

Any description of prior art documents herein, or statements herein derived from or based on those documents, is not an admission that the documents or derived statements are part of the common general knowledge of the relevant art.

For the purposes of description all documents referred to herein are hereby incorporated by reference in their entirety unless otherwise stated.

DETAILED DESCRIPTION

The following detailed description conveys exemplary embodiments of the present invention in sufficient detail to enable those of ordinary skill in the art to practice the present invention. Features or limitations of the various embodiments described do not necessarily limit other embodiments of the present invention or the present invention as a whole. Hence, the following detailed description does not limit the scope of the present invention, which is defined only by the claims.

The present invention provides a radiolabelled material comprising:
(i) a polymer;
(ii) a radioactive isotope; and
(iii) an immobilizing agent;
wherein the immobilizing agent is capable of immobilizing the radioactive isotope on or in the polymer, and wherein the immobilizing agent is a macromolecule comprising electron donating groups.

Immobilizing Agent

The immobilizing agent is a compound which is capable of immobilizing the radioactive isotope on or within the polymer. The immobilizing agent is preferably a macromolecule which comprises electron donating groups, such as groups comprising heteroatoms O, N, S and P. Preferably, the electron donating group is —OH.

Preferably, the immobilizing agent is an aromatic polyol, a phenol or polyphenol compound. More preferably, the immobilizing agent is a phenol or polyphenol compound.

The term "polyphenol" is understood to mean a natural, synthetic or semi-synthetic organic compound characterised by the presence of large numbers of (i.e., multiple) phenol structural units.

In particular, a polyphenol is understood to mean a compound with a molecular weight of 500-4000 Da, more than twelve phenolic hydroxide groups and 5 to 7 aromatic groups per 1000 Da.

Suitable polyphenol immobilizing agents of the invention include tannins, tannic acid, and theaflavin-3-gallate.

Tannic acid is non-toxic and has a high biological tolerance, and is a preferred immobilizing agent of the present invention.

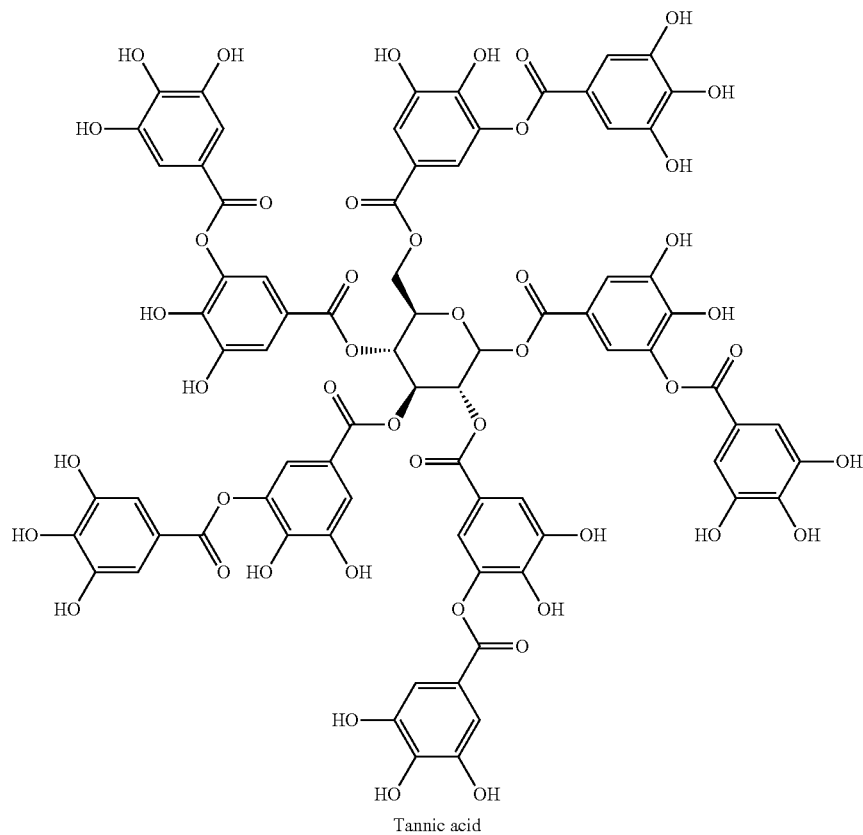 [SMILES: O=C(OC[C@H]1OC(OC(=O)c2cc(O)c(O)c(OC(=O)c3cc(O)c(O)c(O)c3)c2)[C@H](OC(=O)c2cc(O)c(O)c(OC(=O)c3cc(O)c(O)c(O)c3)c2)[C@@H](OC(=O)c2cc(O)c(O)c(OC(=O)c3cc(O)c(O)c(O)c3)c2)[C@@H]1OC(=O)c1cc(O)c(O)c(OC(=O)c2cc(O)c(O)c(O)c2)c1)c1cc(O)c(O)c(OC(=O)c2cc(O)c(O)c(O)c2)c1]

Tannic acid

Single-photon emission computed tomography (SPECT) is a nuclear medicine tomographic imaging technique using gamma rays and is able to provide true 3D information. The information is often presented as cross-sectional slices through the patient. Due to the gamma-emission of the isotope, it is possible to see where the radiolabelled material has accumulated in the patient's body. Such a true 3D representation can be helpful in tumour imaging.

Positron emission tomography (PET) is a nuclear medicine imaging technique that produces a 3D image and has a higher sensitivity than traditional SPECT imaging. The system detects pairs of gamma rays emitted indirectly by a positron-emitting radionuclide (tracer), which is introduced into the body. 3D images of tracer concentration within the body are then constructed by computer analysis and the 3D imaging is often accomplished with the aid of a CT X-ray scan performed on the patient during the same session, in the same machine. Positron-emitting isotopes can also be used in conjunction with CT to provide 3D imaging of the anatomical distribution of a labelled medical device.

The immobilizing agent of the present invention is able to immobilize one or more radioactive elements on the polymer, each producing different levels and types of radiation (such as gamma and beta radiation) and having different half-lives. Therefore, the radiolabelled material of the invention may comprise a radioactive isotope to enable imaging (such as by SPECT or PET) and/or a radioactive isotope to enable therapy. Therefore, the same polymer particles may be employed in the investigative imaging procedure (i.e. as "mimic" particles) and the therapeutic procedure. In this way, the mimic particles can accurately predict the organ distribution of the therapeutic particles to give an accurate estimate of the number of patients deemed suitable for therapeutic particles.

Further, the immobilizing agent of the present invention is able to simultaneously immobilize one or more radioisotopes suitable for imaging and therapy on the polymer. Imaging techniques can be employed which can determine the precise site of the therapeutic radiation exposure in the patient's body and therefore enables the determination of the effectiveness of the treatment and the necessity for future treatments.

The immobilizing agent substantially reduces the leaching of the radioactive isotope from the polymer. Therefore, sufficient specific activity (radioactivity per unit mass) can be obtained on the polymer microspheres for imaging and therapy, such that the number of microspheres can be minimized. This avoids using an excessive number of microspheres to achieve an imaging or therapeutic dose, which could otherwise degrade imaging resolution and therapeutic efficacy by producing local accumulations or clumps of microspheres in vessels. Further, the reduction in leaching of the therapeutic isotope from the microspheres reduces unintended tissue damage in non-target organs.

For example, the immobilizing agent of the present invention is able to bind the important and clinically useful isotopes of Gallium, Ga-67 (for SPECT imaging) and Ga-68 (for PET imaging) to the polymer. Ga-67 produces gamma radiation as it decays. Therefore, the position of the radiation can be confirmed using a SPECT or scintigraphic image made from the photon emission, which uses a gamma camera to detect the gamma radiation from the radioactive isotope. Ga-68 produces positron emission as it decays. Positron emission tomography (PET) is a more recent nuclear medicine imaging method that provides superior imaging resolution to SPECT and is also gradually becoming more commonly used.

Ga-67 exhibits a half-life of 3.26 days. This relatively long half-life is advantageous as there is more time available between manufacture of the radiolabelled material and the administration to the patient before there is significant loss of activity in the radioactive element, therefore leading to lower associated costs.

In particular, the immobilizing agent is able to bind an optimal imaging isotope (such as for SPECT and/or PET) and an optimal therapeutic isotope (such as a soft or hard beta source) in the one material. Preferably, the immobilizing agent is able to bind at least two isotopes having comparable half-lives. This is advantageous because both the imaging properties and the therapeutic property of the radiolabelled material are then similarly preserved over the time period required for transport and distribution to the point of use. For example, Ga-67 has a half-life of 3.26 days that is comparable with the half-life of the therapeutic isotope Y-90 (2.67 days).

Preferred combinations of the present invention include Ga-67 (SPECT imaging) and Lu-177 (beta therapy); Ga-67 (SPECT imaging) and Y-90 (beta therapy); and Ga-68 (PET imaging) and Y-90 (beta therapy). A most preferred example is Ga-67 and Y-90.

The ability to immobilize different radioactive isotopes also achieves a more versatile cancer treatment program. The immobilizing agent can be tailored to suit the radioactive isotope to be immobilized and the isotope or isotope combinations can conveniently be chosen to suit the type of cancer and the site of the tumour in the body.

The immobilizing agent may be halogenated, for example with iodine substitution, in order to make the radiolabelled material X-ray opaque. For example, if the immobilizing agent is tannic acid, it is readily iodinated at the rate of 11 atoms of iodine per molecule of tannic acid (Gardner W M and Hodgson M A, J. Chem. Soc., Trans. 1909; 95:1819-1827). Use of such radiocontrast agents aids in visualizing the location of the immobilizing agent in organs during administration, and may be used to improve the visibility of internal bodily structures, such as tumours, in X-ray imaging techniques including computed tomography (CT) or radiography (commonly known as X-ray imaging).

The immobilizing agent may also be radiolabelled with other clinically useful non-metal isotopes, such as by halogenation, to provide imaging and/or therapy. Preferably, the immobilizing agent may be radiolabelled to provide SPECT and/or PET imaging. The immobilizing agent may be radiolabelled using isotopes such as I-123, I-124, I-125, I-131, I-132, F-18 and At-211. Preferably, the immobilizing agent may be radiolabelled using I-131.

The radiolabelled immobilizing agent may provide both imaging capabilities and radiotherapy. In particular, the immobilization agent, such as tannic acid, may be iodinated with an isotope of iodine that provides radiotherapy (I-131 and I-132; I-131 may be used for beta therapy) and/or SPECT imaging (I-123 and I-131).

The radiolabelled material of the present invention may comprise the combination of a radioactive metal isotope (for example, Y-90 for use in therapy) and a radiolabelled immobilizing agent (for example, tannic acid iodinated with I-123 for use in imaging).

The immobilizing agent functions at acid pH, so the radioactive isotope is not displaced from the polymer anionic groups. In addition, the immobilizing agent enables the radioactive isotope to be retained on the polymer over a pH range 4 to 7 and in vivo after exposure to blood.

Autoclaves are often used in medicine to sterilize equipment and supplies by subjecting them to high pressure saturated steam at 121° C. for around 15-20 minutes. Advantageously, the presence of the immobilizing agent minimises loss of radioactive isotopes from the polymer of the present invention during autoclave conditions specified by the Therapeutic Goods Administration (TGA, the regulatory authority for therapeutic goods in Australia) and therefore this provides a reliable and safe method of sterilization.

Polymer

The polymer of the present invention may be any polymer having a surface that is biocompatible with blood (i.e. does not promote blood coagulation by the so-called intrinsic pathway, or thrombosis by promotion of platelet adhesion).

The polymer of the present invention may be a synthetic polymer. Preferably, the synthetic polymer is a cationic exchange resin comprising anionic substituent groups, such as sulfate, sulfonate, carboxylate and phosphate groups in order to bind the cationic radioactive metal isotopes.

For example, the synthetic polymer may be any blood biocompatible polymer known in the art, including but not limited to polystyrene, polystyrene sulfonate, polypropylene, polytetrafluorethylene (PTFE), expanded polytetrafluoroethylene (EPTFE), polyurethane, polyvinyl chloride, polyamides, teflon, polyester, polyethylene terephthalate, poly(butylene terephthalate) (PBT), poly(ethylene oxide) (PEO), polylactide (PLA), polyglycolide (PGA), poly(lactide-co-glycolide) (PLGA), poly(ε-caprolactone), polydioxanone, trimethylene carbonate, polyanhydride, and poly[bis (p-carboxyphenoxyl) propane:sebacic acid. Preferably, the synthetic polymer is polystyrene sulfonate.

In particular, polytetrafluorethylene (PTFE), expanded polytetrafluoroethylene (EPTFE), polyurethane, polyvinyl chloride, polyamides, polystyrene and teflon may be employed as polymers in the present invention.

Synthetic polymers which may be used for vascular grafts include polyester, for example polyethylene terephthalate, polyurethane, and polytetrafluoroethylene.

The synthetic polymer may be adhered to or in the form of a catheter, a fibre, rod or filament, wire, membrane, wafer, mesh, gauze, porous sponge, tube, stent, bead, capsule, microparticles, microspheres, nanoparticles and liposomes. Preferably, the synthetic polymer is in the form of microspheres, seeds, a stent, catheter, wire or a wafer. Stents may be used with radioisotopes for endovascular brachytherapy to prevent reocclusion during the short post-operative period, in which the stent includes a radioisotope to inhibit proliferation of smooth muscle cells.

The polymer microspheres are appropriately sized to provide lodgement at limiting diameters of an organ's capillary network. The microspheres preferably have a median diameter of between 2 and 200 microns, of between 10 to 50 microns, up to 35 microns or between 25 and 35 microns. Examples of radionuclide-containing microspheres are described in U.S. application Ser. No. 11/192,299.

Selective Internal Radiation Therapy (SIRT) involves the administration of polymer microspheres into the blood supply of the target organ via a catheter and therefore delivers targeted, internal irradiation therapy directly to the tumour. Preferably, the microspheres lodge in the vasculature of the tumour. This provides the advantage that the radiation is preferentially delivered in a slow and continuous manner to the target organ. It is also possible to manipulate the blood supply using appropriate drugs, in order to increase the level of radiation to the target organ (rather than surrounding healthy tissues). As previously mentioned, the immobilizing agent of the present invention substantially prevents leaching and so once the microspheres have reached the target organ, the appropriate radiation is delivered to the tumour.

The polymer microspheres for use in the present invention includes those used in the manufacture of SIR-spheres® (SIR-spheres® is a registered trademark of Sirtex SIR-Spheres Pty Ltd) microspheres, which are resin based microspheres comprised of polystyrene sulfonate.

The polymer may be halogenated, for example with iodine substitution, in order to make the radiolabelled material X-ray opaque. Use of such radiocontrast agents aids in visualizing the location of the polymer in organs during administration, and may be used to improve the visibility of internal bodily structures, such as tumours, in X-ray imaging techniques including computed tomography (CT) or radiography (commonly known as X-ray imaging).

The polymer may also be radiolabelled with other clinically useful non-metal isotopes, such as by halogenation, to provide imaging and/or therapy. Preferably, the polymer may be radiolabelled to provide SPECT and/or PET imaging. For example, the polymer may be radiolabelled using isotopes such as I-123, I-124, I-125, I-131, I-132, F-18 and At-211. Preferably, the polymer may be radiolabelled using I-131.

The radiolabelled polymer may provide both imaging capabilities and radiotherapy. In particular, the polymer may be iodinated with an isotope of iodine that provides radiotherapy (I-131 and I-132; I-131 may be used for beta therapy) and/or SPECT imaging (I-123 and I-131).

The radiolabelled material of the present invention may comprise the combination of a radioactive metal isotope (for example, Y-90 for use in therapy) and a radiolabelled polymer and/or immobilizing agent (for example, tannic acid iodinated with I-123 for use in imaging).

In a similar way to that of the immobilizing agent, the polymer may also be derivatised, such as by halogenation, in order to make the radiolabelled material X-ray opaque. Use of such X-ray contrast agents aid in visualizing the location of the immobilizing agent in organs during administration, and may be used to improve the visibility of internal bodily structures, such as tumours, in X-ray imaging techniques including computed tomography (CT) or radiography (commonly known as X-ray imaging).

Radioactive Isotope

The radioactive isotope of the present invention enables imaging and/or therapy. Preferably, the imaging includes SPECT imaging, and/or PET imaging.

The radioactive isotopes of the present invention may include radioactive metal or semi-metal isotopes. Preferably, the radioactive isotopes are water soluble metal cations.

Examples of suitable radioactive metal isotopes of the present invention include Ac-225, At-211, Au-198, Bi-212, Bi-213, Co-57, Cr-51, Cu-64, Cu-67, Dy-165, Er-169, F-18, Fe-59, Ga-67, Ga-68, Gd-153, Ho-166, I-123, I-124, I-125, I-131, I-132, In-111, Ir-192, Lu-177, Pd-103, Rb-81, Rb-86, Re-186, Re-188, Ru-103, Sc-47, Sm-153, Sn-117m, Sr-89, Tb-161, Tc-99m, Tl-201, Y-90, Yb-169 and Zr-89.

In particular, the radioactive isotope of the present invention includes those elements in the group XIII (the Boron Family) of the periodic table, which includes Ga (see Tables 1 and 2), In (see Table 5) and Tl (see Table 6).

In particular, preferred radioactive isotopes include Ga-67, Ga-68, Y-90, In-111 and Tl-201. Most preferably, radioactive isotopes are Ga-67 (see Tables 1 and 2) and In-111 (see Table 5).

The radioactive isotope of the present invention also includes transition metals, such as Lu-177 (see Table 4), Y-90 (see Table 3), Cu-64, Cu-67 and Tb-161. Preferably, the radioactive isotope is Lu-177 or Y-90.

The isotopes of the present invention are understood to also include the parent isotopes.

The radiolabelled material of the present invention may comprise a combination of at least two radioactive isotopes to enable imaging and/or therapy. The combination of radioactive isotopes may be selected from Ga-68 and Lu-177; Ga-67 and Y-90; Ga-68 and Y-90; In-111 and Y-90; Tl-201 and Y-90; Lu-177 and Y-90 and Ga-67 and Tb-161.

Preferably, the radioactive isotope of the present invention is Y-90 and the polymer and/or immobilizing agent is radiolabelled with I-123, I-131 or F-18; the radioactive isotope is Lu-177 and the polymer and/or immobilizing agent is radiolabelled with F-18; or the radioactive isotope is Tb-161 and the polymer and/or immobilizing agent is radiolabelled with F-18.

The present invention may further include the use of at least one non-radioactive, non-toxic carrier metals. These carrier metals aid in substantially decreasing leaching of the radioactive isotope from the polymer. For example, the carrier metal may be selected from Bi, Fe, Ga, and Y (see, e.g., FIG. 1), e.g., the carrier metal may be Bi, or may be Fe, or may be Ga, or may be Y. A preferred example is non-radioactive gallium (a natural mixture of Ga-69 and Ga-71), which can be used in combination with the Ga-67 radioisotope, or in combination with other radioactive isotopes, such as Lu-177, Y-90, In-111 or Tl-201.

In particular, the non-radioactive carrier metal enables MRI imaging (for example Fe) or X-ray contrast imaging (for example Bi).

Further examples of carrier metals include the trivalent bismuth, which additionally provides X-ray contrast in the microspheres, so that they can be imaged in CT.

Carrier metals may also further enhance stability during autoclaving and storage in the days before use (for example, in at least 3 days before use). A preferred example is a heavy transition metal such as iron, which forms a very insoluble stable complex with tannic acid on the polymer microsphere. The insoluble iron complex advantageously helps retain the metal isotope and immobilizing agent within the polymer microsphere (see FIG. 2) and can also enable MRI imaging. A further example of a carrier metal is yttrium, which forms a very stable insoluble complex with tannic acid (see FIG. 1).

The radiolabelled material according to the present invention may emit gamma, beta, and/or positron radiation.

The present invention also provides a process for making a radiolabelled material as described above comprising:
(i) mixing the polymer as described above in the section entitled 'Polymer' with a radioactive isotope as described above in the section entitled 'Radioactive Isotope';
(ii) optionally washing the resulting mixture;
(iii) further adding an immobilizing agent as described above in the section entitled 'Immobilizing Agent'; and
(iv) optionally washing the resulting mixture.

The present invention also provides for use of an immobilizing agent to immobilize a radioactive isotope on or in a polymer, wherein the immobilizing agent, the radioactive isotope and the polymer are as described above.

The present invention also provides for use of a radiolabelled material according to the invention and as described above for the manufacture of a medicament for the treatment of cancer and/or for radiation imaging.

The present invention further provides for a method for the treatment of cancer, the method comprising administering an effective amount of the radiolabelled material according to the invention and as described above to a patient in need thereof.

The cancer may be a primary or secondary liver cancer or a primary kidney cancer.

The present invention further provides for a medical device comprising a radiolabelled material according to the invention and as described above.

The medical device may be a microsphere, seed, stent, catheter, wire or wafer.

It will be appreciated by persons of ordinary skill in the art that numerous variations and/or modifications can be made to the present invention as disclosed in the specific embodiments without departing from the spirit or scope of the present invention as broadly described. The present embodiments are, therefore, to be considered in all respects as illustrative and not restrictive.

EXAMPLES

The present invention will now be described with reference to specific examples, which should not be construed as in any way limiting.

Example 1

Tannic Acid Reactions with Metal Ions

While there is historical data for ferric tannate as a form of black ink, and for bismuth tannate as a pharmaceutical, reactions of tannic acid with metal cations now used as radioisotopes in modern medicine are less known.

Figure 2:
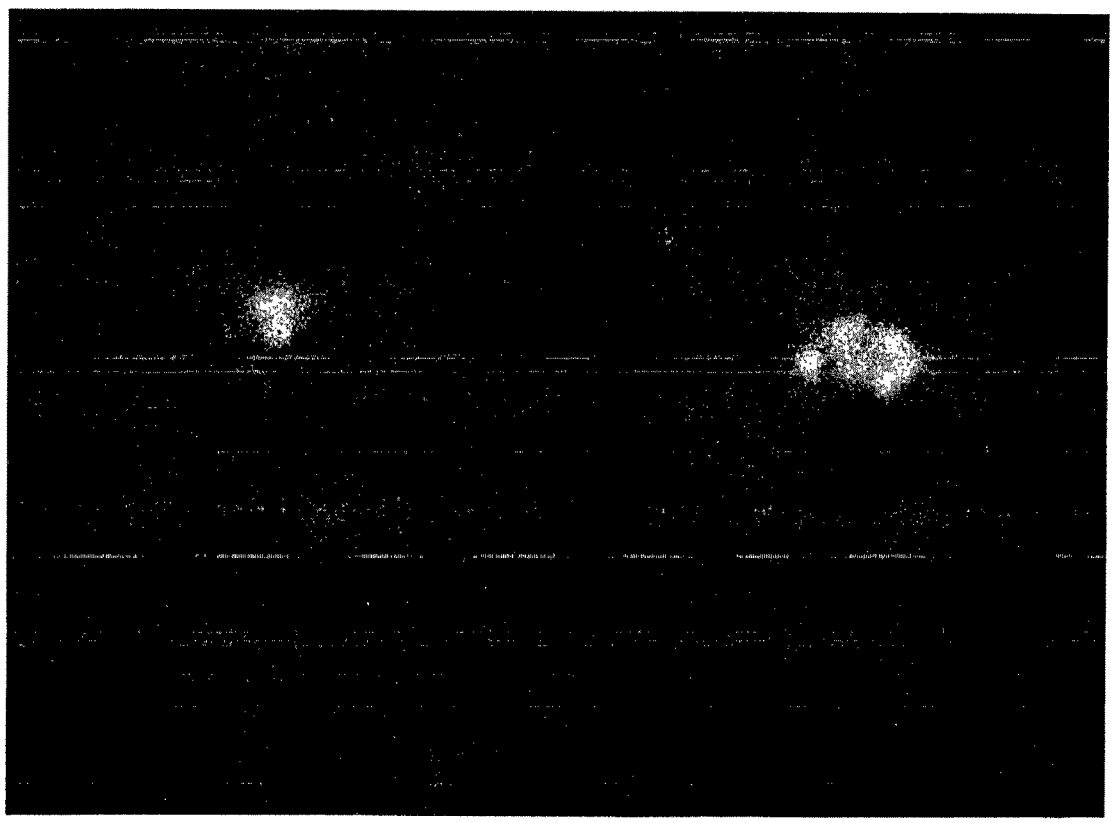
FIG. 2 shows a direct comparison of whole rabbit gamma camera images after hepatic artery catheter instillation in the liver of Ga-67 labelled microspheres (25 mg; 150 MBq Ga-67) made using non-radioactive Gallium as the carrier metal and with the addition of ferric chloride ($FeCl_3$, 3 µg/mg resin; right) and without addition of $FeCl_3$ (left). It is noted that there is slight leakage in vivo of the radioactive isotope label from the polymer microspheres made without addition of $FeCl_3$ compared to the marked retention of the radioactive isotope label on the polymer microspheres made with addition of $FeCl_3$. Other anatomical features, e.g. vertebral column, became weakly visible when the polymer microspheres used were made without addition of $FeCl_3$.

FIG. 1 shows the results of adding 1.0 M solutions (15 µL) of the corresponding metal chlorides (all from Sigma-Aldrich) in 1.0 M HCL to a 3 mM solution of tannic acid (5 mL; Sigma-Aldrich) at room temperature. Bismuth ions immediately formed a heavy cream precipitate; ferric ions immediately formed a heavy blue-black colloid, and yttrium ions at first gave no visible change, but within 3 min formed a grey turbid colloid. Gallium, gadolinium and lutetium ions showed no change, even on long standing (see FIG. 1). The same experiment with copper ions also showed no visible change, but complexation of copper ions with tannic acid is known in the literature (Kraal, P. et al. Chemosphere 2006; 65: 2193-2198). Thus, some metal cations rapidly complex with tannic acid and even form visible precipitates, while others form complexes that remain soluble depending on the conditions (McDonald, M. et al. J Agric Food Chem 1996; 44:599-606).

Example 2

Process for Making Radiolabelled Microspheres

Step 1: Prewash polystyrene sulfonate microspheres (50 mg) in pure water, using low speed centrifugation and resuspension in 3 rinses of water (5 mL each). Finally resuspend in 1 mL water.

Step 2: Add to the washed microspheres Ga-67, In-111, Lu-177, Tl-201 or Y-90 isotope (e.g. 10 to 10,000 MBq) as a solution of the corresponding chloride salt in 0.1 mL of 0.1 M HCl solution. Then add a 1 M solution of the chloride salt of a non-radioactive carrier metal (e.g. Bi, Fe, Ga, or Y) to a final concentration of 3 mM. Mix gently for 1 hour at room temperature.

Step 3: Wash in 3 rinses of water (5 mL each), using low speed centrifugation and resuspension. Finally resuspend in 1 mL water. Measure the bound radioactivity.

Step 4: Add 4 mL of freshly made tannic acid solution (4 mM) and mix gently for 1 hour at room temperature.

Step 5: Wash in 3 rinses of water (5 mL each), using low speed centrifugation and resuspension. Finally resuspend in 3 mL water. Measure the bound radioactivity.

Step 6: Autoclave at standard sterilizing conditions of 120° C. for 20 min.

Example 3

Radiochemical Grade Ga-67 Radiolabelled Microspheres

Table 1 below shows the labelling of microspheres with Ga-67 using radiochemical grade Ga-67 chloride solution (Nordion) as the isotope source. Ga-67 was immobilized on polystyrene sulfonate microspheres (50 mg; Sirtex) as described in Example 2, using non-radioactive gallium trichloride (Sigma-Aldrich) as carrier and tannic acid (Sigma-Aldrich) as the immobilizer. Table 1 shows the percentage of initial isotope loading that was immobilized on the microspheres at the referenced Steps in Example 2.

TABLE 1

Gallium-67 binding to microspheres with tannic acid fixation

| Preparation # | Ga-67 Activity added at Step 2 (MBq)/ 50 mg resin | % Activity Bound after Step 3 | % Activity Bound after Step 5 | % Bound after Step 6* |
|---|---|---|---|---|
| 1 | 46 | 96.0 | N/A | 84.4 |
| 2 | 392 | 87.3 | 84.0 | 81.8 |
| 3 | 380 | 93.8 | 90.8 | 88.4 |
| 4 | 585 | 95.1 | 90.3 | 89.0 |
| 5 | 542 | 99.4 | 95.6 | 93.2 |
| 6 | 512 | 96.9 | 92.3 | 82.4 |
| 7 | 532 | 97.8 | 93.4 | 83.9 |
| 8 | 502 | 95.0 | 92.0 | 80.3 |
| 9 | 413 | 98.6 | 97.2 | 94.6 |
| 10 | 522 | 98.2 | 95.3 | 93.3 |
| 11 | 437 | 96.7 | 94.1 | 91.8 |
| 12 | 481 | 98.2 | 96.5 | 95.4 |
| 13 | 396 | 100 | 96.5 | N/A |
| Average | 442 | 96.4 | 93.2 | 88.2 |
| Standard Deviation | | 3.3 | 3.7 | 5.5 |

*underestimate due to incomplete transfer

Example 4

Clinical Grade Ga-67 Radiolabelled Microspheres

For clinical preparations using Ga-67, it is necessary to use a GMP clinical grade source of the isotope. This is supplied commercially as a more dilute Ga-67 solution and contains sodium chloride and a sodium citrate buffer. The presence of citrate changes the pH and buffer properties of the Ga-67 source. Therefore, a procedure for Ga-67 radiolabelling of microspheres using a dilute GMP clinical solution containing citrate buffer is as follows:

After washing the polystyrene sulfonate microspheres (50 mg; Sirtex) according to Step 1 in Example 2, the microspheres were acidified with 1.0 M HCl (1.0 mL) before addition of the Ga-67 solution (3.5 mL) at Step 2. No carrier was used in these preparations. After mixing gently for 1 hour at room temperature the process was continued at Step 3 in Example 2.

Table 2 below shows the radiolabelling of microspheres with Ga-67 using clinical grade (GMP) Ga-67 supplied as the dilute injectable solution containing sodium chloride and sodium citrate (Lantheus). Table 2 shows the percentage of initial isotope loading that was immobilized on the microspheres at the referenced Steps in Example 2. Also shown are the results of leach tests on the microsphere preparations, performed 7 days after Step 6. In this test, the autoclaved microspheres were spun down, resuspended in 0.15 M sodium chloride (5 mL) and incubated at room temperature for 30 min before centrifugation and measurement of the activity in the supernatant. The supernatant activity is shown as a percentage of the total activity.

TABLE 2

Clinical Gallium-67 binding to microspheres with tannic acid fixation

| Preparation # | Ga-67 Activity added at Step 2 (MBq)/ 50 mg resin | % Ga-67 Bound after Step 3 | % Ga-67 Bound after Step 5 | % activity in supernatant after Leach Test |
|---|---|---|---|---|
| 1 | 258 | 81.6 | 77.4 | 5.4 |
| 2 | 194 | 85.3 | 83.3 | 3.5 |
| 3 | 163 | 95.5 | 91.9 | 1.5 |
| 4 | 200 | 92.3 | 90.2 | 2.5 |
| 5 | 392 | 89.0 | 85.7 | 3.6 |
| 6 | 141 | 86.6 | 85.7 | 1.9 |
| 7 | 141 | 87.9 | 85.7 | N/A |
| 8 | 279 | 88.7 | 88.0 | 1.9 |
| 9 | 259 | 85.3 | 86.0 | N/A |
| Mean | 225 | 88.02 | 86.07 | 2.9 |
| Standard Deviation | 81 | 4.1 | 4.2 | 1.4 |

Example 5

Y-90 Radiolabelled Microspheres

Table 3 below shows the radiolabelling of microspheres with the medically important Y-90 isotope, using radiochemical grade Y-90 chloride solution (Perkin-Elmer) as the source of isotope. Y-90 was immobilized on polystyrene sulfonate microspheres (50 mg; Sirtex) as described in Example 2, using tannic acid (Sigma Aldrich) as the immobilizer. Table 3 shows the percentage of initial isotope loading that was immobilized on the microspheres at the referenced Steps in Example 2. Also shown are the results of leach tests on the microsphere preparations, performed 7 days after Step 6. In this test the autoclaved microspheres were spun down, resuspended in 0.15 M sodium chloride (5 mL) and incubated at room temperature for 30 min before centrifugation and measurement of the activity in the supernatant. The supernatant activity is shown as a percentage of the total activity.

TABLE 3

Yttrium-90 binding to microspheres with tannic acid fixation

| Preparation # | Y-90 Activity added at Step 2 (MBq)/ 50 mg resin | % Y-90 Bound after Step 3 | % Y-90 Bound after Step 5 | % Activity in supernatant after Leach Test |
|---|---|---|---|---|
| 1 | 42.3 | 95.9 | 95.7 | 0 |
| 2 | 41.7 | 97.6 | 97.5 | 0.1 |
| Mean | | 96.8 | 96.6 | 0.05 |

This result establishes that polystyrene sulfonate microspheres can be stably labelled with the medically important Y-90 that is used clinically for internal radiotherapy and ablation of tumors.

Example 6

Lu-177 Radiolabelled Microspheres

Table 4 shows the labelling of microspheres with Lu-177. The isotope was immobilized to polystyrene sulfonate microspheres (50 mg) as described in Example 2, using non-radioactive gallium trichloride as carrier and tannic acid as the immobilizer. Table 4 shows the percentage of initial isotope loading that was immobilized on the microspheres at each step in the overall process.

TABLE 4

Lutetium-177 binding to microspheres with tannic acid fixation

| Preparation # | Lu-177 Activity added (MBq)/ 50 mg resin | % Activity Initially Bound after Step 3 | % Activity Bound after Step 5 | % Bound after Step 6* |
|---|---|---|---|---|
| 1 | 50 | 99.9 | 99.4 | 90.0 |
| 2 | 49 | 99.8 | 98.2 | 83.0 |
| Average | | 99.9 | 98.8 | 86.5 |

*underestimate due to incomplete transfer

Example 7

In-111 Radiolabelled Microspheres

Table 5 shows the labelling of microspheres with In-111. The isotope was immobilized to polystyrene sulfonate microspheres (50 mg) as described in Example 2, using non-radioactive gallium trichloride as carrier and tannic acid as the immobilizer. Table 5 shows the percentage of initial isotope loading that was immobilized on the microspheres at each step in the overall process.

TABLE 5

Indium-111 binding to microspheres with tannic acid fixation

| Preparation # | In-111 Activity added (MBq)/ 50 mg resin | % Activity Initially Bound after Step 3 | % Activity Bound after Step 5 | % Bound after Step 6* |
|---|---|---|---|---|
| 1 | 35 | 97.7 | 105.4 | 93.5 |
| 2 | 33 | 100.0 | 103.4 | 92.0 |
| Average | | 98.9 | 104.4 | 92.8 |

*underestimate due to incomplete transfer

Example 8

Tl-201 Radiolabelled Microspheres

Table 6 shows the labelling of microspheres with Tl-201. The isotope was immobilized to polystyrene sulfonate microspheres (50 mg) as described in Example 2, using non-radioactive gallium trichloride as carrier and tannic acid as the immobilizer. Table 6 shows the percentage of initial isotope loading that was immobilized on the microspheres at each step in the overall process.

TABLE 6

Thallium-201 binding to microspheres with tannic acid fixation

| Preparation # | Tl-201 Activity added (MBq)/ 50 mg resin | % Activity Initially Bound after Step 3 | % Activity Bound after Step 5 | % Activity Bound after Step 6* |
|---|---|---|---|---|
| 1 | 93 | 75.4 | 72.6 | 71.0 |
| 2 | 93 | 72.7 | 69.4 | 66.9 |
| Average | | 74.1 | 71.0 | 69.0 |

*underestimate due to incomplete transfer

The results obtained in Tables 1 to 6 show that the radioisotopes Ga-67 (both radioisotope grade and clinical grade), In-111, and Tl-201 (three members of the so-called Boron family), as well as the transition metal isotopes, Y-90 and Lu-177, are all suitable isotopes for use in the method of Example 2 for radiolabelling polymer microspheres. All of these isotopes except Y-90 are suitable for SPECT imaging, and Lu-177 has the additional advantage that it can be used as a source of therapeutic beta radiation. Y-90 is especially suitable for therapy of tumors with beta radiation.

Comparative Example 9

Binding of Ga-67 on Polystyrene Sulfonate Microspheres without Immobilizing Agent Gallium-67 chloride in 0.1 M HCL solution (15-90 µL; Nordion Inc) was added to washed polystyrene sulfonate microspheres (8 mg; Sirtex Pty Ltd) in water (3 mL). The mixture was equilibrated on a rotary mixer for 1 h at room temperature. The microspheres were then separated by centrifugation and the supernatant aspirated and the gamma radioactivity measured in a Capintec ionisation chamber. The microspheres were then resuspended in 0.15 M NaCl (3 mL) and autoclaved at 120° C. for 20 min. After separation again, the supernatant was aspirated and radioactivity measured. The microspheres were then resuspended in a second aliquot of 0.15 M NaCl (3 mL) and autoclaved a second time. After separation the supernatant was aspirated and the radioactivity measured. The results are shown in Table 7.

TABLE 7

Gallium binding to microspheres without fixation

| Volume of Ga-67 solution [µL] | Radio-activity [MBq] | % activity in supernatant after Ga-67 binding | % activity in supernatant after 1$^{st}$ autoclaving | % activity in supernatant after 2$^{nd}$ autoclaving |
|---|---|---|---|---|
| 15 | 108 | 0.5 | 49.8 | 38.6 |
| 30 | 215 | 0.3 | 66.6 | 23.3 |
| 60 | 436 | 0.6 | 32.0 | 29.4 |
| 90 | 653 | 0.4 | 26.8 | 16.5 |

The results in Table 7 show that while polystyrene sulfonate microspheres can efficiently bind metal cations at low pH, the metal ions are not stably bound and remain exchangeable at increased electrolyte concentration and higher temperature. This does not allow them to be sterilised by autoclaving or used in vivo as a stable source of localised radiation.

This experiment shows the necessity to use an immobilizing agent to complex with and stably immobilize the radioisotope that has been bound on the sulfonated microsphere surface.

The invention claimed is:
1. A radiolabelled material comprising:
(i) a polymer;
(ii) a radioactive isotope; and
(iii) an immobilizing agent;
wherein the polymer is a synthetic polymer, and the synthetic polymer is a cationic exchange resin comprising at least one of a sulfate, sulfonate, carboxylate and phosphate group;
the radioactive isotope is a cationic radioactive isotope;
the immobilizing agent is a macromolecule comprising electron donating groups, said immobilizing agent selected from tannins, tannic acid and theaflavin-3-gallate;

the radioactive isotope is complexed with at least one sulfate, sulfonate, carboxylate or phosphate group of the polymer; and the immobilizing agent is complexed with the radioactive isotope.

2. The radiolabelled material according to claim 1, wherein the immobilizing agent is tannic acid.

3. The radiolabelled material according to claim 1, wherein the polymer is polystyrene sulfonate.

4. The radiolabelled material according to claim 1, wherein the polymer is in the form of particulate microspheres having a median diameter of between 2 and 200 microns.

5. The radiolabelled material according to claim 1, wherein the radioactive isotope is selected from the group consisting of: Ac-225, Au-198, Bi-212, Bi-213, Co-57, Cr-51, Cu-64, Cu-67, Dy-165, Er-169, Fe-59, Ga-67, Ga-68, Gd-153, Ho-166, In-111, Ir-192, Lu-177, Pd-103, Rb-81, Rb-86, Re-186, Re-188, Ru-103, Sc-47, Sm-153, Sn-117m, Sr-89, Tb-161, Tc-99m, Tl-201, Y-90, Yb-169 and Zr-89.

6. The radiolabelled material according to claim 1, wherein the radioactive isotope is Ga-67, In-111, Lu-177, Tl-201 or Y-90.

7. The radiolabelled material according to claim 1 comprising a combination of at least two radioactive isotopes.

8. The radiolabelled material according to claim 7, wherein the combination of radioactive isotopes is selected from the group consisting of Ga-68 and Lu-177; Ga-67 and Y-90; Ga-68 and Y-90; In-111 and Y-90; Tl-201 and Y-90; Lu-177 and Y-90 and Ga-67 and Tb-161.

9. The radiolabelled material according to claim 1, wherein the polymer, the immobilizing agent or both the polymer and the immobilizing agent is radiolabelled with a non-metal radioactive isotope.

10. The radiolabelled material according to claim 9, wherein the polymer, the immobilizing agent or both the polymer and the immobilizing agent is radiolabelled with I-123, I-124, I-125, I-131, I-132, F-18, At-211, or a mixture of any two or more of these.

11. The radiolabelled material according to claim 9, wherein the radioactive isotope is Y-90 and the polymer, the immobilizing agent or both the polymer and the immobilizing agent is radiolabelled with I-123, I-131 or F-18; or the radioactive isotope is Lu-177 and the polymer, the immobilizing agent or both the polymer and the immobilizing agent is radiolabelled with F-18; or the radioactive isotope is Tb-161 and the polymer or immobilizing agent or both the polymer and the immobilizing agent is radiolabelled with F-18.

12. The radiolabelled material according to claim 1, further comprising at least one non-radioactive carrier metal.

13. The radiolabelled material according to claim 12, wherein the non-radioactive carrier metal is selected from the group consisting of Bi, Fe, Ga and Y.

14. The radiolabelled material according to claim 12, wherein the non-radioactive carrier metal is Fe, Bi, or a mixture of both.

15. A process for making a radiolabelled material, said radiolabelled material comprising:
(i) a polymer;
(ii) a radioactive isotope; and
(iii) an immobilizing agent;
wherein the polymer is a synthetic polymer, and the synthetic polymer is a cationic exchange resin comprising at least one of a sulfate, sulfonate, carboxylate and phosphate group;
the radioactive isotope is a cationic radioactive isotope;
the immobilizing agent is a macromolecule comprising electron donating groups, said immobilizing agent selected from tannins, tannic acid and theaflavin-3-gallate;
the radioactive isotope is complexed with at least one sulfate, sulfonate, carboxylate or phosphate group of the polymer; and
the immobilizing agent is complexed with the radioactive isotope;
said process comprising:
(i) mixing the polymer with the radioactive isotope;
(ii) optionally washing the resulting mixture;
(iii) further adding an immobilizing agent; and
(iv) optionally washing the resulting mixture.

16. A method for the treatment of cancer, the method comprising administering an effective amount of a radiolabelled material to a patient in need thereof, the radiolabeled material comprising:
(i) a polymer;
(ii) a radioactive isotope; and
(iii) an immobilizing agent;
wherein the polymer is a synthetic polymer, and the synthetic polymer is a cationic exchange resin comprising at least one of a sulfate, sulfonate, carboxylate and phosphate group;
the radioactive isotope is a cationic radioactive isotope;
the immobilizing agent is a macromolecule comprising electron donating groups, said immobilizing agent selected from tannins, tannic acid and theaflavin-3-gallate;
the radioactive isotope is complexed with at least one sulfate, sulfonate, carboxylate or phosphate group of the polymer; and
the immobilizing agent is complexed with the radioactive isotope.

17. A medical device comprising a radiolabelled material comprising:
(i) a polymer;
(ii) a radioactive isotope; and
(iii) an immobilizing agent;
wherein the polymer is a synthetic polymer, and the synthetic polymer is a cationic exchange resin comprising at least one of a sulfate, sulfonate, carboxylate and phosphate group;
the radioactive isotope is a cationic radioactive isotope;
the immobilizing agent is a macromolecule comprising electron donating groups, said immobilizing agent selected from tannins, tannic acid and theaflavin-3-gallate;
the radioactive isotope is complexed with at least one sulfate, sulfonate, carboxylate or phosphate group of the polymer; and
the immobilizing agent is complexed with the radioactive isotope.

* * * * *

UNITED STATES PATENT AND TRADEMARK OFFICE
CERTIFICATE OF CORRECTION

PATENT NO. : 10,232,062 B2
APPLICATION NO. : 14/901633
DATED : March 19, 2019
INVENTOR(S) : Ross Wentworth Stephens et al.

Page 1 of 1

It is certified that error appears in the above-identified patent and that said Letters Patent is hereby corrected as shown below:

In the Claims

In Column 17, Line 56, in Claim 14, after "Fe," insert -- or --.

Signed and Sealed this
Tenth Day of December, 2019

Andrei Iancu
*Director of the United States Patent and Trademark Office*